US009254500B2

(12) United States Patent
Linnell et al.

(10) Patent No.: US 9,254,500 B2
(45) Date of Patent: Feb. 9, 2016

(54) AEROSOL GENERATION FOR STABLE, LOW-CONCENTRATION DELIVERY

(71) Applicants: Massachusetts Institute of Technology, Cambridge, MA (US); The United States of America as represented by the Secretary of the Navy, Washington, DC (US)

(72) Inventors: Jesse Allen Linnell, Chelmsford, MA (US); Trina Rae Vian, Westford, MA (US); Joseph Renard Morency, Salem, MA (US); Anlong Dai, Riverside, RI (US); Mark Eric Bury, Acton, MA (US); Thomas Sebastian, Waltham, MA (US); Carlos Andres Aguilar, Boston, MA (US); Joseph John Lacirignola, Beverly, MA (US); Jay D. Eversole, Woodbridge, VA (US)

(73) Assignees: Massachusetts Institute of Technology, Cambridge, MA (US); The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/510,262

(22) Filed: Oct. 9, 2014

(65) Prior Publication Data

US 2015/0097048 A1 Apr. 9, 2015

Related U.S. Application Data

(60) Provisional application No. 61/888,737, filed on Oct. 9, 2013.

(51) Int. Cl.
*G01N 15/06* (2006.01)
*B05B 7/04* (2006.01)
(Continued)

(52) U.S. Cl.
CPC .............. *B05B 12/082* (2013.01); *B05B 1/262* (2013.01); *B05B 7/0483* (2013.01); *G01N 15/06* (2013.01); *A61M 15/00* (2013.01); *A61M 2209/02* (2013.01); *G01N 2001/2223* (2013.01)

(58) Field of Classification Search
CPC .. B05B 7/0416; B05B 7/0483; B05B 12/082; G01N 2001/2223; G01N 15/06; G01N 2015/0693; G01N 37/00; A61M 2209/02
USPC ............. 239/8, 11, 13, 69, 71, 135, 338, 399, 239/403; 73/28.01
See application file for complete search history.

(56) References Cited

U.S. PATENT DOCUMENTS

| 5,156,776 A | 10/1992 | Loedding et al. |
| 5,918,254 A | 6/1999 | Bottiger et al. |
| 7,343,782 B2 | 3/2008 | Damer et al. |
| 7,387,038 B2 | 6/2008 | Wei |
| 7,926,741 B2 | 4/2011 | Laidler et al. |

FOREIGN PATENT DOCUMENTS

EP 1436090 B1 12/2006

OTHER PUBLICATIONS

Jesse A. Linnell, et al., "Interim Point Detector Analyzer (IPDA)", AAAR Annual Conference Poster Session, Minneapolis, MN (Oct. 9, 2012).

(Continued)

*Primary Examiner* — Darren W Gorman
(74) *Attorney, Agent, or Firm* — Modern Times Legal; Robert J. Sayre

(57) ABSTRACT

A feed aerosol comprising detectable particles is injected into a mix-enhancing swirler. Diluting gas is also injected into the mix-enhancing swirler and mixed with the feed aerosol in a swirling motion to form an aerosol with a particle concentration no greater than 1,000 particles per liter. The aerosol is then injected into a mixing chamber, where the aerosol is mixed and dried; the inner diameter of the mixing chamber is at least twice as great as that of the swirl chamber. The aerosol is then emitted through a flow straightener that removes swirl from the flow of the aerosol and passed through a delivery conduit, where the particles are detected and counted; and the particle count is compared with a target count. The respective flows of feed aerosol and diluting gas can then be increased or decreased based on a comparison of the particle count with the target count.

19 Claims, 7 Drawing Sheets

(51) Int. Cl.

| | |
|---|---|
| *B05B 12/08* | (2006.01) |
| *B05B 1/26* | (2006.01) |
| *G01N 1/22* | (2006.01) |
| *A61M 15/00* | (2006.01) |

(56) References Cited

OTHER PUBLICATIONS

US Patent and Trademark Office, PCT/US14/59845 International Search Report and Written Opinion (Dec. 24, 2014) (corresponding PCT application).

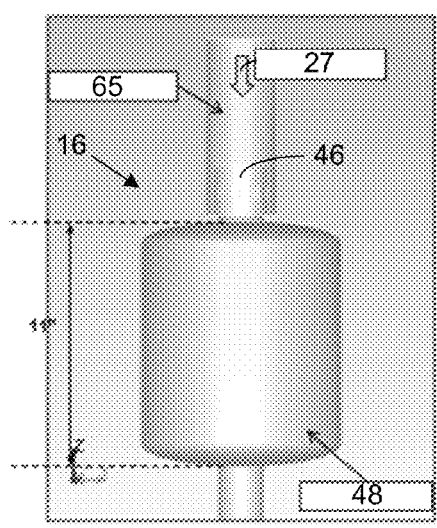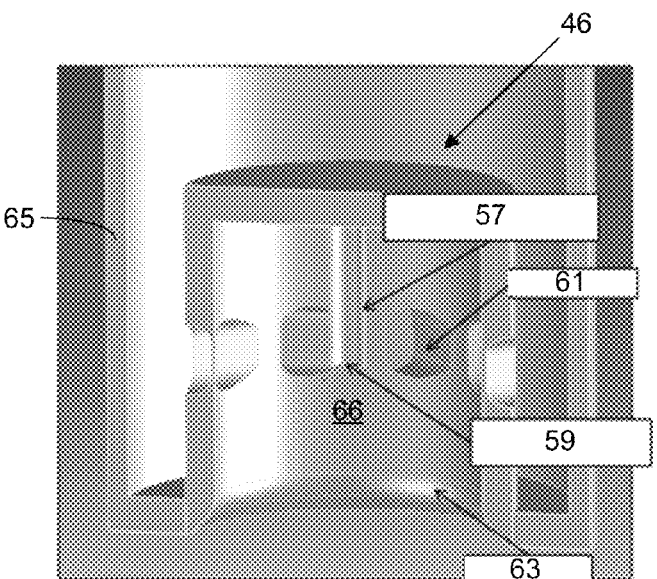
FIG. 7
FIG. 8
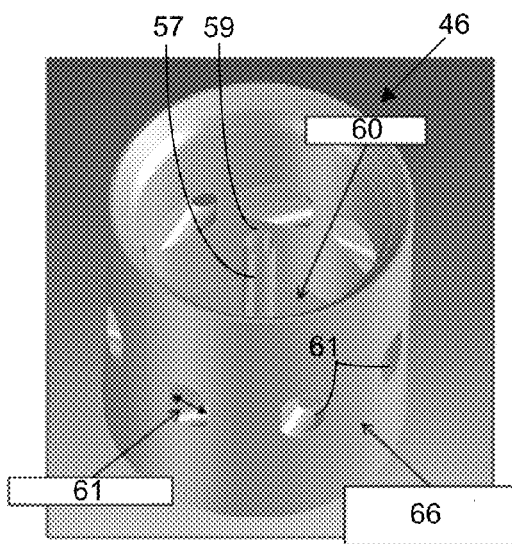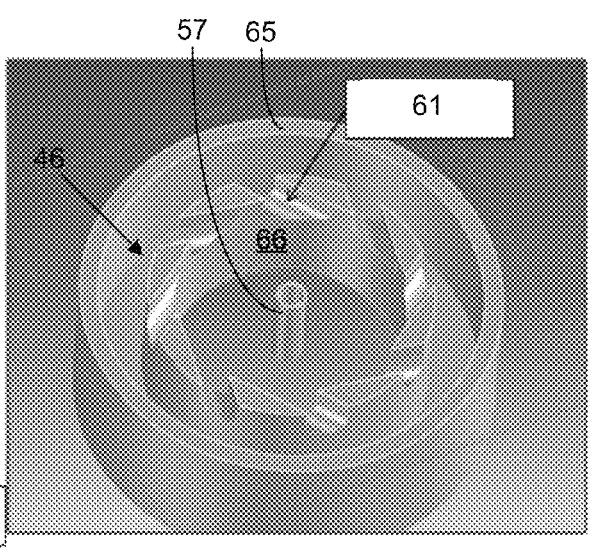
FIG. 9
FIG. 10

AEROSOL GENERATION FOR STABLE, LOW-CONCENTRATION DELIVERY

RELATED APPLICATION

This application claims the benefit of U.S. Provisional Application No. 61/888,737, filed 9 Oct. 2013, the entire content of which is incorporated herein by reference.

GOVERNMENT SUPPORT

This invention was made with government support under Grant No. FA8721-05-C-0002 awarded by the Naval Research Laboratory. The U.S. Government has certain rights in the invention.

BACKGROUND

Using existing methods, particle sensors for measuring the contents of aerosols are tested in a test chamber, where the chamber is filled with a known particle concentration. The readings from the particle sensor can then be compared with the known particle concentration in the chamber to evaluate the accuracy of the particle sensor. This evaluation typically requires exposure of the external surfaces of the particle sensor to the test aerosol, and the particle sensor, therefore, becomes contaminated. Sensor testing can typically only be conducted in the laboratory because of the complexity of the test setup. Additionally, testing typically is unreliable at low particle concentration levels; and the establishment of a stable, low particle concentration is very difficult to achieve. Nevertheless, testing at low concentration levels may be necessary to test sensor limits of detection, which can be important for detecting harmful biological organisms or other toxic items, where detection at very low concentrations levels may be important.

SUMMARY

Methods and apparatus for generating a stable, low-concentration aerosol are described herein. Various embodiments of the apparatus and methods may include some or all of the elements, features and steps described below.

In a method for generating a stable, low-concentration aerosol, a flow of a feed aerosol comprising detectable particles is generated and injected into a mix-enhancing swirler. A flow of a diluting gas is also injected into the mix-enhancing swirler and mixed with the feed aerosol to form a low-concentration aerosol with a particle concentration of no greater than 1,000 particles per liter (e.g., between 10 and 1,000 ppl, or more particularly between 10 and 500, or even more particularly between 10 and 200 ppl). The low-concentration aerosol is injected from the mix-enhancing swirler into an inlet of a mixing chamber, and the low-concentration aerosol is mixed and dried in the mixing chamber. The low-concentration aerosol is then emitted from an outlet of the mixing chamber through a flow straightener that removes swirl from the flow of the low-concentration aerosol and passed from the flow straightener through a delivery conduit, where the particles are detected and counted (e.g., using an isokinetic probe) to produce a particle count that is then compared with a target count. If the particle count is less than the target count, the flow of feed aerosol is increased, and the flow of diluting gas into the mix-enhancing swirler is decreased. If, on the other hand, the particle count is greater than the target count, the flow of feed aerosol is decreased; and the flow of diluting gas into the mix-enhancing swirler is increased. The mixing chamber has a diameter, measured orthogonally to a flow path from the inlet to the outlet, that is at least twice as great as a diameter of the swirl chamber of the mix-enhancing swirler.

An aerosol generator for generating a stable, low-concentration aerosol includes the following components: a source of a feed aerosol, a source of a diluting gas, a mix-enhancing swirler, a mixing chamber, a flow straightener, a delivery conduit, and a particle detector. The mix-enhancing swirler is in communication both with the source of feed aerosol along a first axis and with the source of diluting gas along a second axis oriented at an angle distinct from that of the first axis. The mix-enhancing swirler is configured to generate a swirling low-concentration aerosol formed of the feed aerosol and the diluting gas. The mixing chamber is downstream of the mix-enhancing swirler and is configured to mix and dry the low-concentration aerosol. The in-line flow straightener is configured to straighten the flow of the low-concentration aerosol from the mixing chamber. The delivery conduit is configured to receive the low-swirl flow of the low-concentration aerosol from the flow straightener. Finally, the particle detector is configured to detect and count particles in the flow of low-concentration aerosol through the delivery conduit, wherein the particle detector is in electronic communication with the source of feed aerosol and with the source of diluting gas to control flow of the feed aerosol and the diluting gas based on a count of the particles by the particle detector.

The aerosol generator can further include a purge system that allows the low-concentration aerosol flow to be diverted and dumped into a filter until the precise time when the test aerosol are to be delivered to the system being tested.

BRIEF DESCRIPTION OF THE DRAWINGS

FIG. 1 is a schematic illustration of an embodiment of an aerosol generator 10 for generating a stable, low-concentration aerosol and a particle-detection apparatus under test 20. The aerosol generator 10 includes a high-concentration aerosol generator 12, a diluting gas supply 14, a mixer 16, and a particle detector 18. The system is controlled by a computer 22, which is in electronic communication with the various components to receive data there from and to issue control commands there to.

FIGS. 7 and 8 show an embodiment of the mix-enhancing swirler 46 contained in the mixer 16. The swirler 46 is mounted on a mixing chamber 48 in FIG. 7, which also shows the delivery tube 57 of a Collison nebulizer with an outlet end 59, swirl slots 61 in the inner apertured swirl inducer wall 66 of the swirler 46. The mix-enhancing swirler 46 is shown via a magnified sectional illustration in FIG. 8.

FIG. 9 is a perspective view showing an embodiment of a mix-enhancing swirler 46.

FIG. 10 is a perspective view of the mix-enhancing swirler 46 of FIG. 9 from an opposite perspective and sectioned through the apertures 61.

Figure 1:
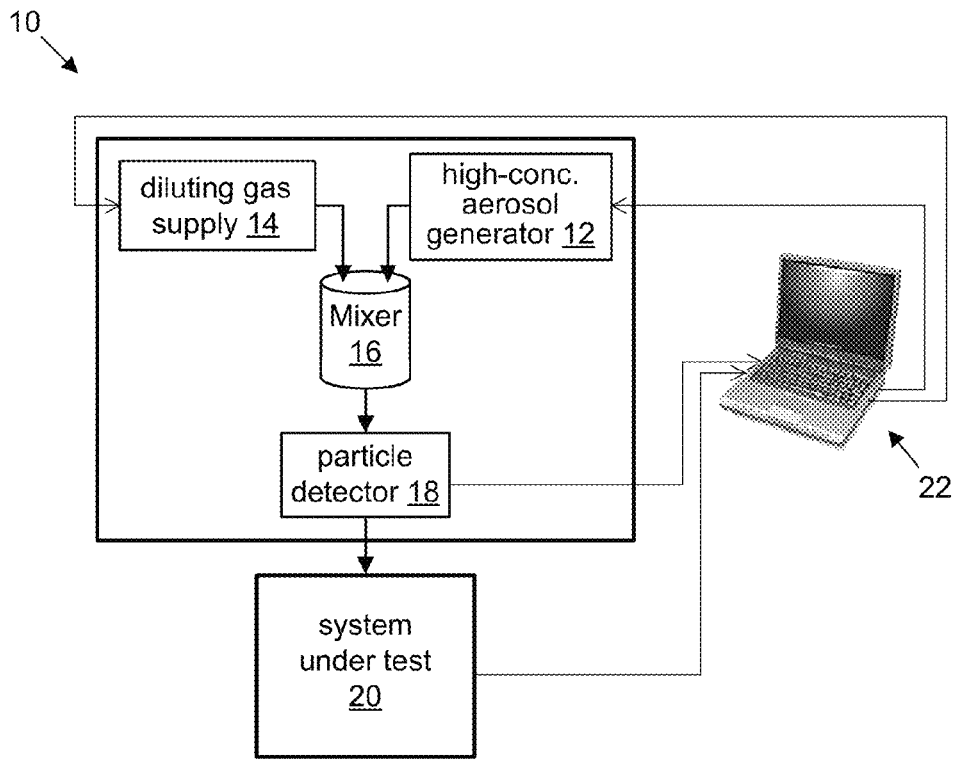
Figure 2:
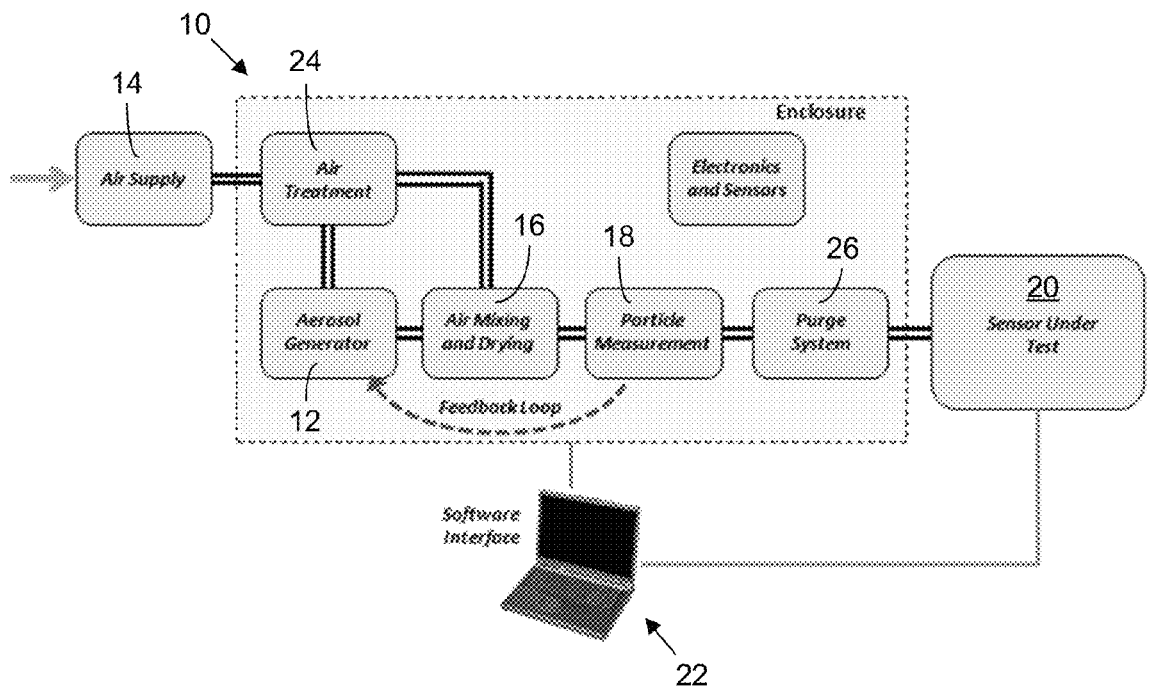
FIG. 2 is a schematic illustration of another embodiment of an aerosol generator 10 for generating a stable, low-concentration aerosol with additional details and components, including a gas purification unit 24 and a purge system 26.

In the accompanying drawings, like reference characters refer to the same or similar parts throughout the different views; and apostrophes are used to differentiate multiple instances of the same or similar items sharing the same reference numeral. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Described herein is a portable aerosol generator 10, an embodiment of which is schematically illustrated in FIG. 1, that can consistently and repeatedly deliver low aerosol concentration in a preprogrammed concentration profile. It is tunable and can deliver a stable concentration down to 10 particles per liter (ppl) and can deliver between 0-150 standard liters per minute (slpm) of test air. The test profile can be delivered at a constant concentration level or as a series of step on/off puffs. The rise time from zero particles to the desired set point concentration is approximately 10 seconds. The apparatus is portable and can operate indoors and outdoors in the laboratory and in the field. It utilizes a feedback control loop to monitor and control aerosol to a <3% confidence averaged over 1 minute at 50 ppl. The unit is software controlled via a computer 22 for a versatile and reprogrammable test profile. There is automated feedback on the test flow rate to match desired chamber pressure or sensor inlet conditions. The low-concentration aerosol generator 10 is of sufficiently low mass to be transportable, e.g., by two men (for example, the aerosol generator 10 can have a weight no greater than 175 pounds). The aerosol generator 10 can be operated at a temperature of, e.g., 40-100° F., and at a humidity of, e.g., 20-80% (i.e., non-condensing). The aerosol generator 10 can also be ruggedized for shipping and handling loads.

Figure 3:
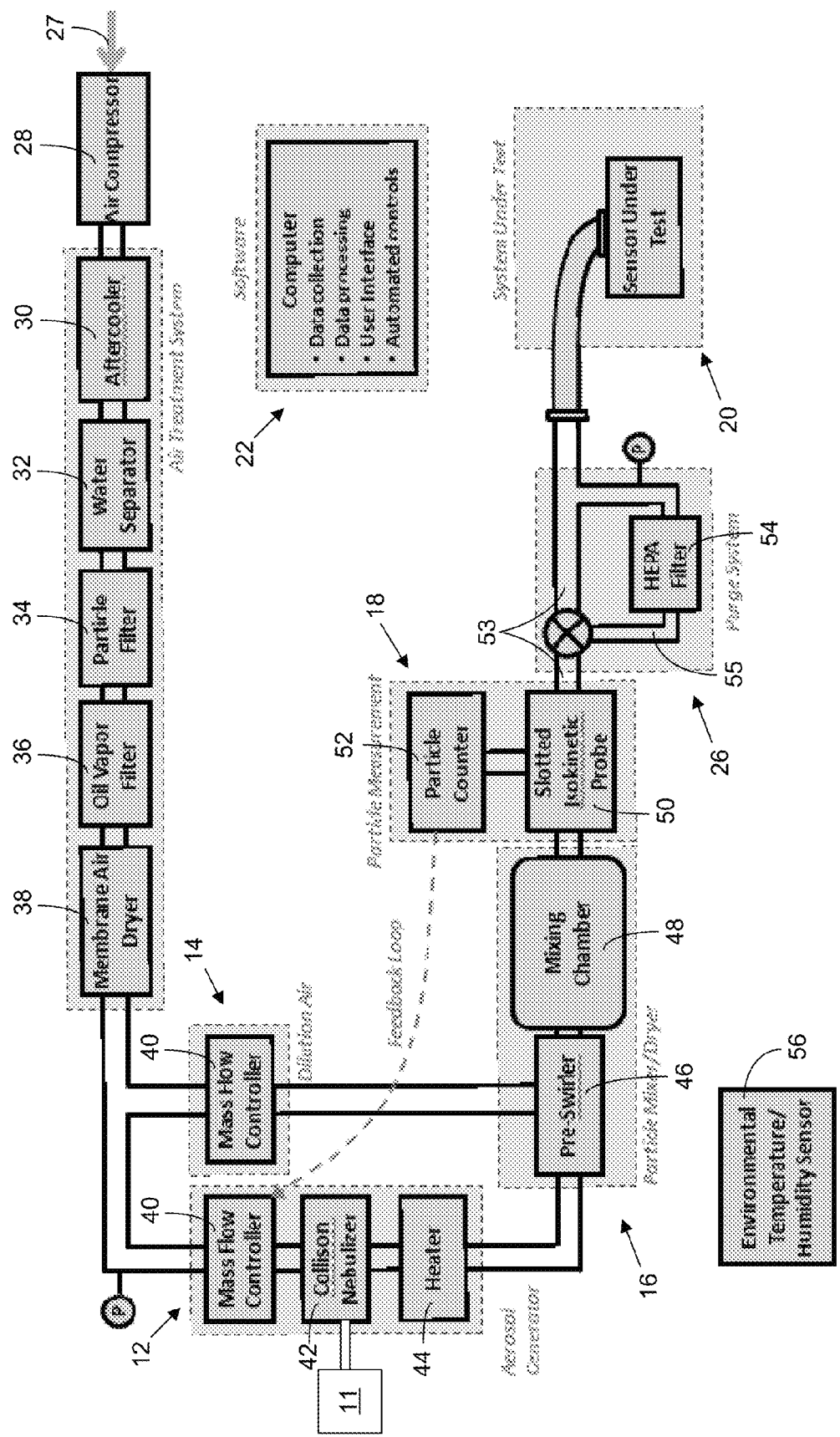
FIG. 3 is a schematic illustration of still another embodiment of an aerosol generator 10 for generating a stable, low-concentration aerosol with additional details and components, including a gas source 27, an air compressor 28, an aftercooler 30, a water separator 32, a particle filter 34, an oil vapor filter 36, a membrane air dryer 38, a mass flow controller 40, a nebulizer 42, a heater 44, a mix-enhancing swirler 46, a mixing chamber 48, a flow straightener 49, a slotted isokinetic probe 50, a particle counter 52, a delivery conduit 53, a high-efficiency particulate air (HEPA) filter 54, and an external environmental temperature/humidity sensor 56.
Figure 4:
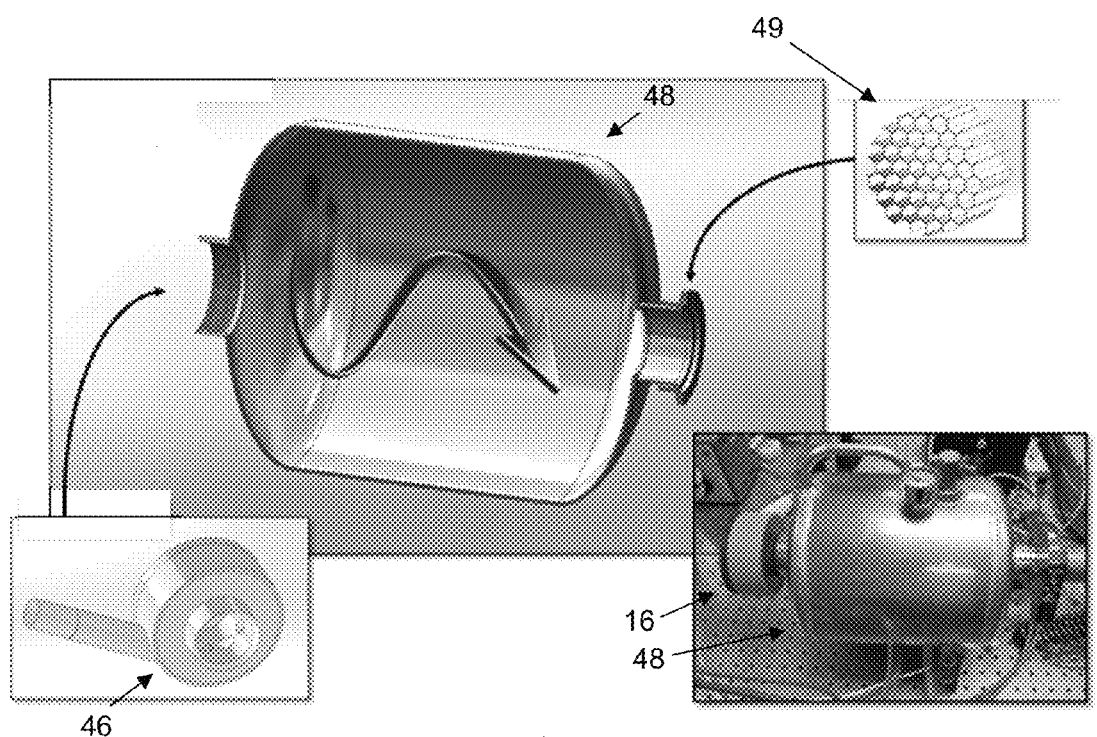
FIG. 4 is an illustration of the mechanical design of an embodiment of the mixing chamber 48 from an aerosol generator, wherein the swirl of aerosol flow in the mixing chamber 48 is illustrated with the arrow seen through the walls of the chamber, which are translucent here for purposes of illustration. Also shown in the insets are the mix-enhancing swirler 46 and the mixer 16 including the swirler attached to the mixing chamber. The flow straightener 49 that is embedded in the output of the mixing chamber 48 and through which the aerosol exits the chamber is shown at upper right.
Figure 5:
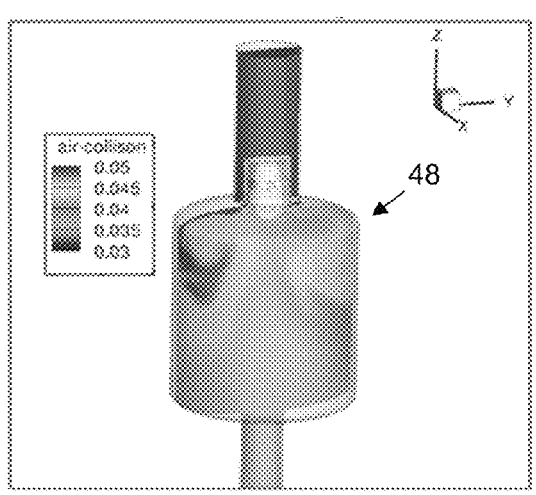
FIG. 5 shows computational fluid dynamics modeling of the mixing chamber, wherein particle mixing is shown via color codings based on particle collisions.
Figure 6:
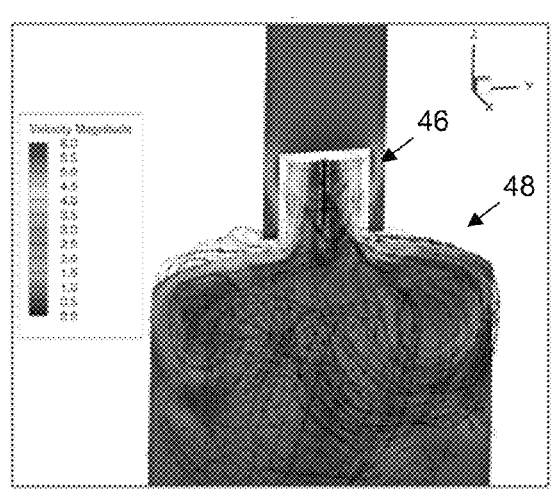
FIG. 6 shows computational fluid dynamics modeling of the mixing chamber, wherein particle trajectories are shown via the illustrated flight paths and velocity magnitudes in the chamber are shown via the color codings.

The apparatus and methods use a compressed gas (e.g., air) supply 27, as shown in FIG. 3, and removes all or substantially all oil vapor and submicron particles while dehumidifying the gas. This conditioned gas is used as dilution gas in order to achieve the low concentration aerosol. The dilution gas is mixed with the output of a high-concentration aerosol generator 12 (including, e.g., a Collison nebulizer 42, an ultrasonic nebulizer, or other type of aerosol generator having a tunable output) in a mix-enhancing swirler 46. The gas flow is then mixed and dried in a high swirl mixing chamber 48. The air flow is then isokinetically sampled and monitored by an optical particle detector 18. The concentration measurement is used with a proportional, integral, derivative controller to tune the high-concentration aerosol generator 12 and to stabilize the particle concentration in the aerosol. The conditioned test air is routed through a filter until the system is in test mode, at which point the test air is redirected to go directly out of the system with minimal loss.

As shown in the schematic illustration of FIG. 1, the low-concentration aerosol generator 10 can include a high-concentration aerosol generator 12 and a diluting gas supply 14. The aerosol from the high-concentration aerosol generator 12 and the diluting gas supply 14 are both fed to a mixer 16, where the aerosol is diluted and then to a particle detector 18 that counts the particles (in liquid or solid form) in the low-concentration aerosol stream. Those counts can be fed to a computer 22 and the concentration of particles in the stream can be determined as a function, e.g., of the flow rate through the particle detector 18.

The computer 22 includes computer-readable instructions non-transiently stored on a computer-readable medium and data including a target particle concentration in the stream. The computer-readable medium is coupled with a computer processor that, when executing the instructions from the computer-readable medium, compares the detected particle readings from the particle detector 18 and compares the counts with the target particle concentration. Of course, as alternatives to targeting a particular particle concentration, one can target an absolute particle count, particle flow rate, etc. The particle detector 18 and computer 22 can likewise compare the readings with the target values. The computer processor is also in electronic communication with an output port for communicating its instructions to components in the system.

If the count from the detector 18 is higher than the target, the computer 22 can generate and transmit an instruction to the high-concentration aerosol generator 12 to reduce the flow rate of the liquid feed 11 through the high-concentration aerosol generator 12 and/or to generate and transmit an instruction to the diluting gas supply 14 to increase the flow rate of diluting gas that is mixed with the high-concentration aerosol.

If, on the other hand, the count from the detector 18 is lower than the target, the computer 22 can generate and transmit an instruction to the high-concentration aerosol generator 12 to increase the flow rate of the liquid feed 11 through the high-concentration aerosol generator 12 and/or to generate and transmit an instruction to the diluting gas supply 14 to decrease the flow rate of diluting gas that is mixed with the high-concentration aerosol.

The low-concentration aerosol stream is ultimately directed from the particle detector 18 to a particle-detection apparatus under test 20. The particle-detection apparatus under test 20 then also generates a particle count, and that count can be compared with the count from the particle detector 18 to evaluate the accuracy and/or sensitivity of particle detection in the particle detection apparatus 20 that is being tested.

In the embodiment shown in FIG. 2, the high-concentration aerosol generator 12 is fed by an air supply that serves both as the diluting gas supply 14 and as the gas for forming the aerosol (in combination with the liquid feed 11) in the high-concentration aerosol generator 12. The air supply delivers air first through an air purification unit 24 that removes impurities from the air, and the output from the air purification unit 24 splits the air flow via respective output conduits (a) to the high-concentration aerosol generator 12 and (b) to the mixer 16 that mixes the diluting gas with the high-concentration aerosol and dries the particles in the aerosol. The resulting aerosol is then directed via conduits through the particle detector 18 and through a purge system 26. The low-concentration aerosol is diverted from the output flow path through the purge system 26 until the particle count is within a narrow margin of error from the targeted setpoint. The purge system 26 can include a high-efficiency particulate (HEPA) filter 54 for removing the particles, as shown in FIG. 3, until the target concentration is reached so that a clean (sharp and accurate) transition can be established between near-instantaneous jumps in the particle count delivered to the particle-detection apparatus under test 20.

In the more-detailed schematic illustration of the aerosol-generator embodiment of FIG. 3, an air supply 27 flows through (in sequence) an air compressor 28, an aftercooler 30, a water separator 32, a particle filter 34, an oil vapor filter 36, a membrane air dryer 38. The air flow is split after the membrane air dryer 38 into separate conduits (a) through a dilution-air path, where the air flows through a mass flow controller 40 and (b) through a high-concentration aerosol generator 12 including, in series, a mass flow controller 40, a Collison nebulizer 42 (into which the liquid feed 11 is also injected to form the aerosol), and a heater 44, which promotes drying of the particles in the aerosol. Pressure gauges in the flow paths are denoted with the letter, P. The two flow paths then reconverge in the mix-enhancing swirler 46 of a mixer 16 that also includes a mixing chamber 48 configured to receive the output of the mix-enhancing swirler 46.

In this embodiment, the resulting diluted aerosol then flows through a slotted isokinetic probe 50 of the particle detector 18 with an electronic particle counter 52 joined with the slotted isokinetic probe 50 and configured to detect the particles in the aerosol passing there through. The aerosol then reaches a ball valve in the purge system 26 that, while the system is in the process of adjusting the flow of the diluting gas from the diluting gas supply 14 and high-concentration aerosol to match the target, can direct the aerosol flow from the delivery conduit 53 to an auxiliary path 55 that includes a HEPA filter 54 for filtering the particles from the stream. Finally, the stream is delivered to a sensor 56 in the particle-detection apparatus under test 20.

Embodiments of the mixing chamber 48 and mix-enhancing swirler 46 are further illustrated in FIG. 4. In this embodiment, the mixing chamber 48 has a three-gallon capacity (11.4 liters) and is 11 inches (28 cm) in length. The mix-enhancing swirler 46 has a compact design and is configured to enhance mixing and recirculation of the aerosolized feed in the gas flow. As shown in FIG. 4, the mix-enhancing swirler 46 generates a swirl in the aerosol flow; and that swirl (as shown by the arrow) is transmitted through the mixing chamber 48. Mounted in the output of the mixing chamber 48, however, is a flow straightener 49 includes narrow, elongated passages (e.g., in a honeycomb structure in the illustrated embodiment) that remove the swirl and substantially straighten the flow of the low-concentration aerosol as it exits the mixing chamber 48 to thereby prepare the aerosol flow for sampling in the particle detector 18.

Computational fluid dynamics modeling of the mixing chamber 48 are shown in FIG. 5, where particle mixing is shown via color codings based on particle collisions. Meanwhile, computational fluid dynamics modeling of the mixing chamber 48 are shown in FIG. 6, wherein particle trajectories are shown via the illustrated flight paths and velocity magnitudes in the chamber 48 are shown via the color codings.

An embodiment of the mix-enhancing swirler 46 is illustrated in FIGS. 7 and 8. The swirler 46 is mounted on a mixing chamber 48 in FIG. 7 and shown via a magnified sectional illustration in FIG. 8. The inner diameter of the pipe 65 through which the diluting gas flows into the inner apertured swirl inducer wall 66 is 3.2 inches (8.1 cm), and the inner diameter of the mixing chamber 48 is 9 inches (22.9 cm) in this embodiment. Accordingly, the inner diameter of the mixing chamber 48 is more than twice as great as the inner diameter of the mix-enhancing swirler 46 and can be, e.g., at least three to five times or greater.

A perspective view showing an embodiment of the inner apertured swirl inducer wall 66 of a mix-enhancing swirler 46 is provided in FIG. 8. In this particular embodiment, the inner diameter of the delivery tube 57 from the Collison nebulizer 42, through which the liquid feed 11 for the aerosol is delivered, is 0.25 inches (0.64 cm); the end 59 of the Collison nebulizer delivery tube 57, from which the liquid feed 11 is released, is 1.25 inches (3.18 cm) above the entrance to the mixing chamber 48. The rounded flare 63 at the mating surface of the mix-enhancing swirler 46 is also illustrated here.

A perspective view of the mix-enhancing swirler 46 is provided in FIG. 9, while a view of the inner apertured swirl inducer wall 66 sectioned through the apertures is shown in FIG. 10. As shown in these figures, the drop from the mating flange 72 of the mix-enhancing swirler 46 to the swirl chamber top plate 60 is 2.25 inches (5.72 cm); the width of the slot apertures is 0.25 inches (0.64 cm); and the apertured wall of the swirl inducer 66 has an inner diameter of 1.939 inches (4.93 cm) and an outer diameter of 2.375 inches (6.03 cm). The eight slot apertures are uniformly distributed around the circumference of the swirl inducer wall 66 (at 45° angular increments).

Figure 11:
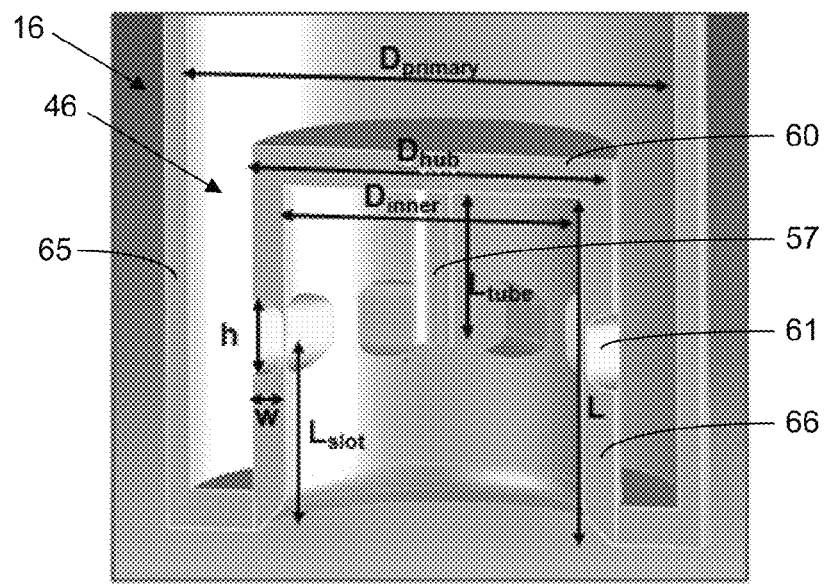
FIG. 11 is a sectional illustration of an embodiment of a mix-enhancing swirler 46 in a mixer 16 with dimensional indications.

In the embodiment of the mix-enhancing swirler 46 illustrated in FIG. 11, the inner diameter of the primary diluting gas delivery pipe 65 ($D_{primary}$) is 3.2 inches (8.1 cm), wherein the primary diluting gas delivery pipe 65 forms the outer swirl chamber wall 62. Meanwhile, the inner diameter of the apertured swirl inducer wall 66 ($D_{inner}$) is 1.939 inches (4.93 cm); and the outer diameter of that body ($D_{hub}$) is 2.375 inches (4.93 cm).

In this embodiment, the ratio of the entrance annular area (3.61 in² or 23.3 cm²) to the "swirl slot effective flow area" (i.e., eight passages in the apertured swirl inducer wall 66 at 0.11 in² per passage to produce a cumulative aperture area of 0.88 in² or 5.7 cm² total) is 4.1, where the entrance annular area is the toroidal section between $D_{primary}$ and $D_{hub}$. This ratio can vary, e.g., anywhere from 2 to well over 10; the ratio impacts pressure loss and flow uniformity. Maintaining a ratio of at least 4 between the toroidal area and the area of the aperture passages can promote substantially even flow through every aperture.

In this embodiment, the swirl chamber height, L, is 2.25 inches (5.72 cm); the slot centerline location in the swirl chamber, $L_{slot}$, is 1.25 inches (3.18 cm); the slot height, h, is 0.5 inches (1.3 cm); the lot width, w, is 0.218 inches (0.554 cm); the ratio, w/h, is 0.44 (decreasing this ratio will decrease swirl generation); and the particle tube distance, $L_{tube}$, is 1 inch (2.5 cm).

Figure 12:
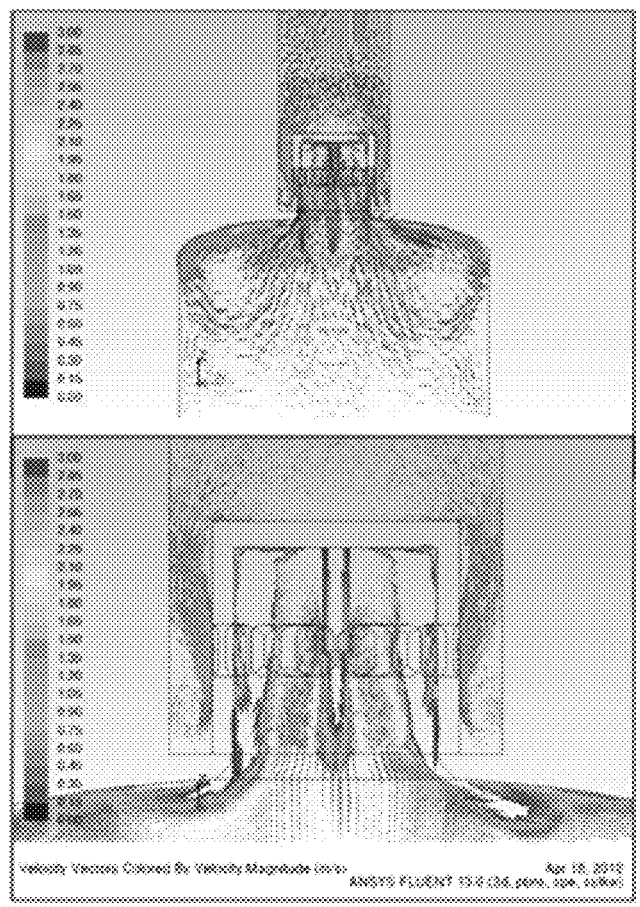
FIG. 12 is an illustration of the mixing chamber showing velocity vectors colored by velocity magnitude.

In the illustration of FIG. 12, velocity vectors in the mixing chamber 48 are shown and are colored as a function of velocity magnitude. In this embodiment, the primary flow rate of the diluting gas into the mix-enhancing swirler 46 is 80.5 L/min (1.61 g/sec at 1.2 kg/m³), and the flow rate through the Collison nebulizer 42 is 2.8 L/min (0.06 g/sec at 1.2 kg/m³). The generated swirl number, S, is 0.88. Higher swirl will lead to higher residences times in the drying chamber. A swirl, S, above ~0.6 can advantageously be used to promote recirculation. The rounded flair entrance 63 at the output of the mix-enhancing swirler 46, where it meets the mixing chamber 48, induces flow attachment due to the Coandă effect.

Figure 13:
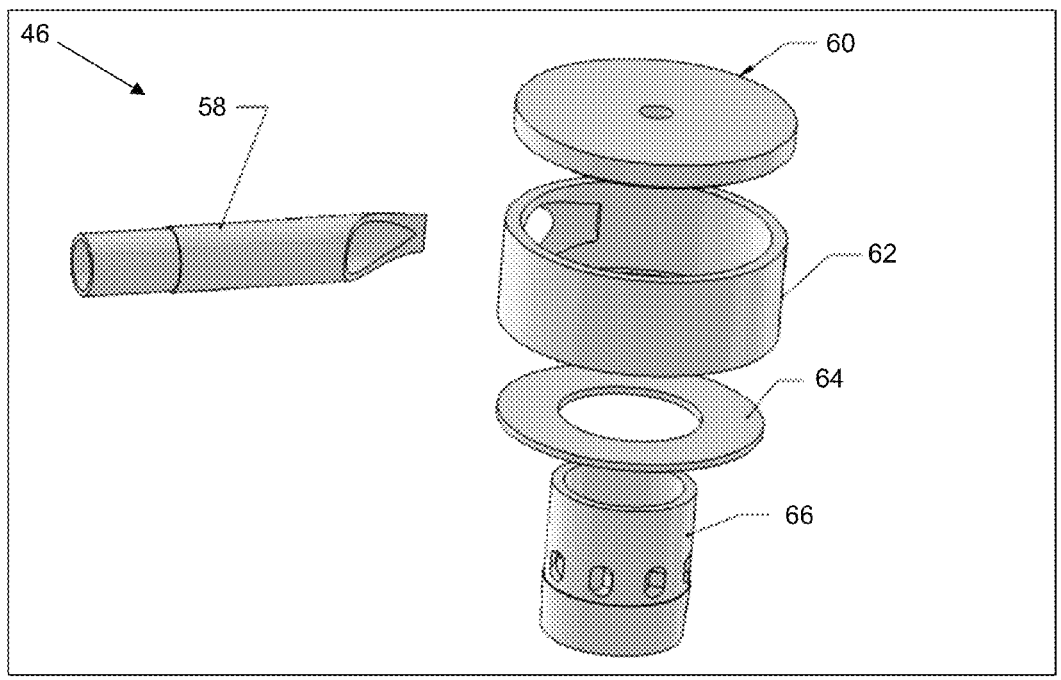
FIG. 13 is an exploded perspective view of an embodiment of the mix-enhancing swirler, showing the swirler input pipe 58, swirl chamber top plate 60 and bottom plate 64, outer swirl chamber wall 62, and inner apertured swirl inducer wall 66.

An exploded perspective view of an embodiment of the mix-enhancing swirler 46, showing the swirler input pipe 58, the swirl chamber top plate 60 and bottom plate 64, the outer swirl chamber wall 62, and the inner apertured swirl inducer wall 66, is provided as FIG. 13. These parts can be joined by sealant (e.g., epoxy, polyvinyl chloride cement or other) to provide an air-tight seal at the seams. The mix-enhancing swirler 46 can be assembled by (1) slipping the swirl chamber bottom plate 64 over the inner apertured swirl inducer wall 66; (2) attaching the outer swirl chamber wall 62 to the swirl chamber bottom plate 64; (3) fastening the swirl chamber top plate 60 to the outer swirl chamber wall 62 and to the inner apertured swirl inducer wall 66, ensuring that a good seal is obtained between both walls; and (4) sliding the swirler input pipe 58 into the outer swirl chamber wall 62.

Figure 14:
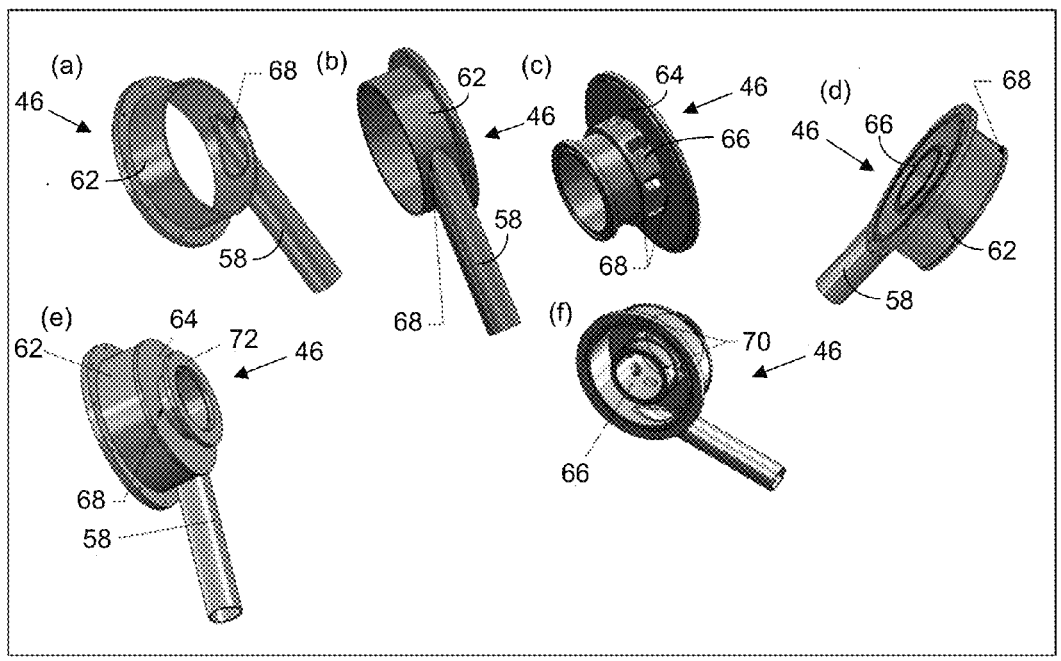
FIG. 14 illustrates steps (a-f) in the assembly of the mix-enhancing swirler 46, showing the seams 68 where welds are made in each step.

Additional steps in a method for assembly of the mix-enhancing swirler 46 are illustrated in FIG. 14. The swirler input pipe 58 is aligned with the orifice in the outer swirl chamber wall 62 and placed in flush contact with the surfaces defining the orifice; the seam 68 at the juncture can then be welded, as shown in step (a). If the seam 68 is accessible on the outer surface of the outer swirl chamber wall 62, as shown in step (b), the weld can be inserted at the seam 68 on the outer surface. The swirl chamber bottom plate 64 is then contacted with the inner apertured swirl inducer wall 66, as shown in step (c), and tack welded in at least three places along the seam 68 around the circumference of the inner apertured swirl inducer wall 66 between the apertures 61. As shown in steps (c) and (d), the outer swirl chamber wall 62 with the swirler input pipe 58 attached, as shown in steps (a) and (b), is placed onto the swirl chamber bottom plate 64 with the inner aperture swirl inducer wall 66 attached, as shown in step (c) and welded along the seam 68 to obtain a seal.

An aluminum flange 72 is then placed onto the swirl chamber bottom plate 64, as shown in step (e) of FIG. 14, and welded around the entire seam 68 to obtain an air-tight seal. Finally, the flatness of the sealing surfaces 70, as shown in step (f), is checked to ensure a tight seal when mounted to the mixing chamber 48. A difference in height of less than 0.010 inches (0.025 cm) over the entire surface is targeted (and the mix-enhancing swirler 46 may be rejected if it does not meet that standard). Some machining may be employed if required to remove distortion due to welding.

Figure 15:
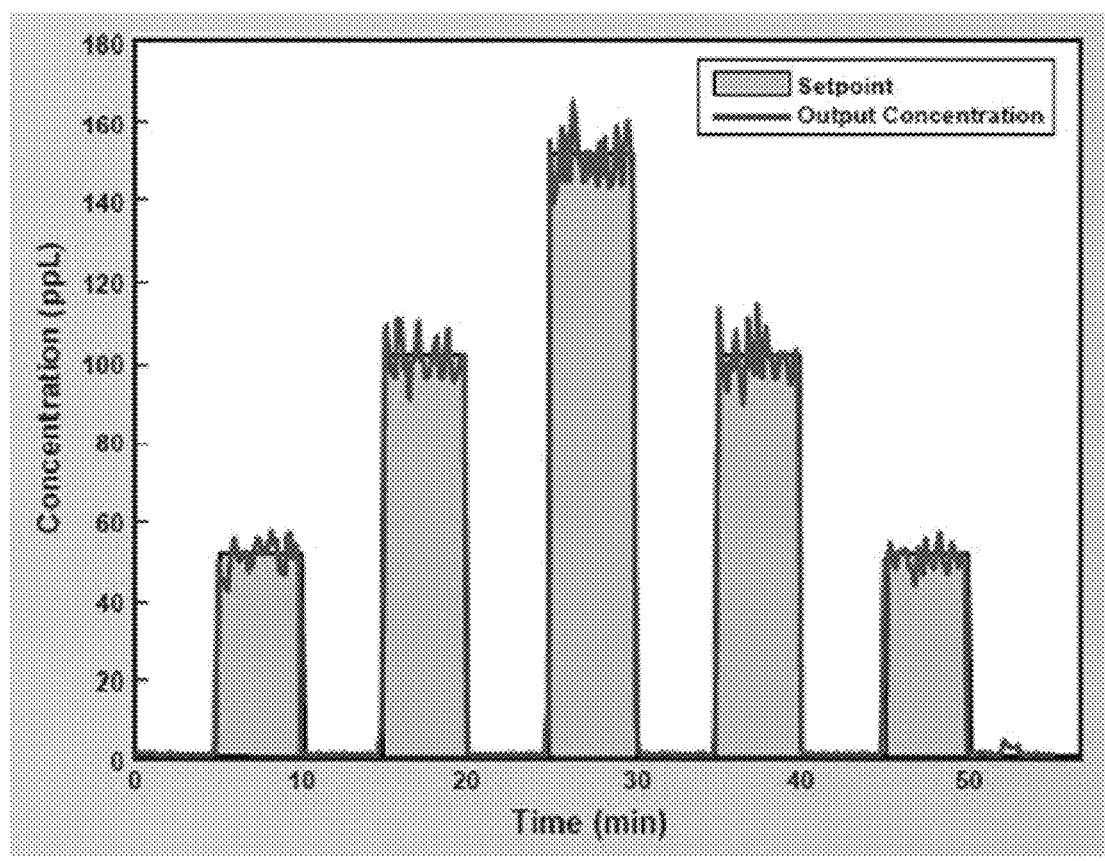
FIG. 15 is a plot showing the demonstrated capability of the low-concentration aerosol generator, wherein the measured aerosol output concentration is plotted against the targeted setpoint.

The demonstrated capability of the low-concentration aerosol generator 10, described herein, is evidenced in the plot of FIG. 15, where the measured aerosol output concentration from a low-concentration aerosol generator 10 is plotted against the targeted setpoint as a function of time. Particle setpoints include 50 ppL, 100 ppL, and 150 ppL. The close fit demonstrates the system's ability to reproducibly and accurately deliver low aerosol concentrations. This system offers automated/programmable operation and electronic feedback control on aerosol concentration.

Exemplary applications for the apparatus and methods described herein include, but are not limited to, the following: use as a sensor (for challenging and calibration of sensors in the laboratory and in the field); aerosol generation (for laboratory and field aerosol generation); sensor studies and chamber studies, indoors and outdoors; animal exposure research (controlled delivery of an aerosol to animals during testing); and pharmaceuticals delivery (controlled delivery of medications).

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10_{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A method for generating a stable, low-concentration aerosol, comprising:
   generating a flow of a feed aerosol comprising detectable particles;
   injecting the flow of feed aerosol into a mix-enhancing swirler;
   injecting a flow of a diluting gas into the mix-enhancing swirler and mixing with the feed aerosol in a swirling motion in a swirl chamber of the mix-enhancing swirler to form a low-concentration aerosol with a particle concentration of no greater than 1,000 particles per liter;
   injecting the low-concentration aerosol from the mix-enhancing swirler into an inlet of a substantially cylindrical mixing chamber;
   mixing and drying the low-concentration aerosol in the mixing chamber;
   emitting the low-concentration aerosol from an outlet of the mixing chamber through a flow straightener that removes swirl from the flow of the low-concentration aerosol;
   passing the low-concentration aerosol from the flow straightener through a delivery conduit;
   detecting and counting the particles in the delivery conduit to produce a particle count;
   comparing the particle count with a target count;
   if the particle count is less than the target count, increasing the flow of feed aerosol and decreasing the flow of diluting gas into the mix-enhancing swirler; and
   if the particle count is greater than the target count, decreasing the flow of feed aerosol and increasing the flow of diluting gas into the mix-enhancing swirler,
   wherein the mixing chamber has an inner diameter, measured orthogonally to a flow path from the inlet to the outlet, that is at least twice as great as an inner diameter of the swirl chamber of the mix-enhancing swirler.

2. The method of claim 1, further comprising:
   injecting the low-concentration aerosol from the delivery conduit into a particle-detection apparatus;
   again detecting and counting the particles in the low-concentration aerosol, this time with the particle-detection apparatus; and
   comparing the particle count from the particle-detection apparatus with the particle count taken in the delivery conduit to evaluate the accuracy of particle detection and counting in the particle-detection apparatus.

3. The method of claim 1, wherein the feed aerosol is generated with a nebulizer.

4. The method of claim 1, wherein the particle concentration in the low-concentration aerosol is in a range from 10-500 particles per liter.

5. The method of claim 4, wherein the particle concentration in the low-concentration aerosol has a noise level no greater than 6% averaged over one minute at 10 ppl.

6. The method of claim 4, wherein the particle concentration in the low-concentration aerosol has a noise level no greater than 2% averaged over one minute at 100 ppl.

7. The method of claim 1, wherein the flow of feed aerosol is injected into the mix-enhancing swirler along a first axis, wherein the flow of diluting gas is injected into the mix-enhancing swirler along a second axis, and wherein the first axis is substantially orthogonal to the first axis.

8. The method of claim 7, wherein the mix-enhancing swirler comprises a substantially cylindrical outer swirl chamber wall, and wherein the diluting gas is injected at a perimeter of the swirl chamber at an angle that is substantially tangential to the outer swirl chamber wall.

9. The method of claim 8, wherein the mix-enhancing swirler further comprises an inner apertured swirl inducer that defines an inner channel into which the feed aerosol is injected and an outer annular channel around which the diluting gas swirls, and wherein the inner apertured swirl inducer further defines apertures through which the diluting gas passes from the outer annular channel to the inner channel where the diluting gas dilutes the feed aerosol to form the low-concentration aerosol.

10. The method of claim 1, wherein the flow straightener defines a plurality of parallel flow channels.

11. The method of claim 1, wherein the particles are detected and counted in the delivery conduit as the low-concentration aerosol flows through the conduit at a rate of at least 28.3 liters per minute.

12. The method of claim 1, wherein the particle count is measured over a window of at least 30 seconds.

13. The method of claim 12, wherein the particle count is compared with the target count at increments that are shorter than the window over which the particles are counted to produce the particle count.

14. The method of claim 1, wherein the flows of feed aerosol and diluting gas are controlled using a proportional-integral-differential feedback controller.

15. The method of claim 1, wherein the particles include a pharmaceutical compound, and further comprising delivering the low-concentration aerosol from the delivery conduit to a living organism in which the pharmaceutical compound will produce a beneficial effect at the low concentration.

16. The method of claim 1, wherein the particles include a compound that is harmful to an organism, and further comprising delivering the low-concentration aerosol from the delivery conduit to a living organism in which the compound will produce a harmful effect at the low concentration, the method further comprising evaluating toxicity or other adverse effects on the organism from exposure to the compound in the low-concentration aerosol.

17. The method of claim 1, further comprising:
diverting the low-concentration aerosol to a purge section and filtering particulates from the low-concentration aerosol in the purge section while the flows of the feed aerosol and the diluting gas are adjusted until the particle count in the low-concentration aerosol matches the target count; then
redirecting the flow of low-concentration aerosol from the purge section to an outlet of the delivery conduit.

18. The method of claim 1, wherein the particles are detected and counted using an isokinetic probe.

19. An aerosol generator for generating a stable, low-concentration aerosol, the aerosol generator comprising:
a source of a feed aerosol;
a source of a diluting gas;
a mix-enhancing swirler in communication both with the source of feed aerosol along a first axis and with the source of diluting gas along a second axis oriented at an angle distinct from that of the first axis, wherein the mix-enhancing swirler is configured to generate a swirling low-concentration aerosol formed of the feed aerosol and the diluting gas;
a mixing chamber in communication with the mix-enhancing swirler and configured to mix and dry the low-concentration aerosol;
a flow straightener in connection with the mixing chamber and configured to straighten flow of the low-concentration aerosol from the mixing chamber;
a delivery conduit configured to receive the straightened flow of the low-concentration aerosol from the flow straightener; and
a particle detector configured to detect and count particles in the low-concentration aerosol flow through the delivery conduit, wherein the particle detector is in electronic communication with the source of feed aerosol and with the source of diluting gas to control flow of the feed aerosol and the diluting gas based on a count of the particles by the particle detector.

* * * * *